United States Patent [19]
Cullen et al.

[11] Patent Number: 4,748,186
[45] Date of Patent: May 31, 1988

[54] S-TRIFLUOROBUTENYL DERIVATIVES AND PESTICIDAL USES THEREOF

[75] Inventors: Thomas G. Cullen, Milltown; Anthony J. Martinez, Hamilton Square; Jacob J. Vukich, Mount Holly, all of N.J.

[73] Assignee: FMC Corporation, Philadelphia, Pa.

[21] Appl. No.: 880,421

[22] Filed: Jun. 30, 1986

[51] Int. Cl.$^4$ .................. C07C 119/18; C07C 155/08; A01N 37/00; A01N 47/10
[52] U.S. Cl. ..................................... 514/478; 558/243; 558/2; 558/4; 558/235; 558/236; 514/508; 514/512
[58] Field of Search .................. 558/243, 2, 4, 235, 558/236; 514/478, 508, 512

[56] References Cited
U.S. PATENT DOCUMENTS

3,510,503  5/1970  Brokke et al. ..................... 558/243
3,658,901  4/1972  Timmons et al. ................... 558/243

FOREIGN PATENT DOCUMENTS

0175332  3/1986  European Pat. Off. ............. 558/243

*Primary Examiner*—John M. Ford
*Assistant Examiner*—Robert C. Whittenbaugh
*Attorney, Agent, or Firm*—Patrick C. Baker; H. Robinson Ertelt

[57] ABSTRACT

S-trifluorobutenyl thiocarbonic acid esters of the formula

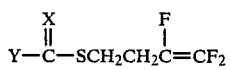

and salts thereof,
wherein X is $R^1N$ or S and Y is RS or $R^3R^2N$;
wherein R is a metal or a radical selected from alkyl, cycloalkylalkyl, halocycloalkylalkyl, alkenyl, haloalkyl, haloalkenyl, alkynyl, alkoxyalkyl, alkylthioalkyl, alkoxycarbonylalkyl, halophenoxyalkyl, trialkylsilylalkyl, (vinyl)dialkylsilylalkyl, (allyl)dialkylsilylalkyl, 2-chlorothiophene-5-ylmethyl, phenylalkyl, halophenylalkyl, nitrophenylalkyl, haloalkylphenylalkyl, dialkyl-2,3-dihydrobenzofuran-7-yl, [2-methyl-(1,1'-biphenyl)-3-yl]methyl, 3-phenoxybenzyl, phenylthioalkyl, halophenylthioalkyl, dialkylphosphoryl, dialkylthiophosphoryl, dialkylisoxazolylalkyl and thienylisoxazolylalkyl;
wherein $R^1$ is alkyl, cycloalkyl, cyano, dialkyl-2,3-dihydrobenzofuran-7-yl, halophenyl, halophenylalkyl, haloalkoxyphenyl, pyridinyl, halopyridinyl, alkyl-1,3,4-thiadiazolyl, haloalkyl-1,3,4-thiadiazolyl, benzothiazolyl, dialkyloxazolyl or thiazolinyl;
wherein $R^2$ is hydrogen or alkyl; and
wherein $R^3$ is alkyl, haloalkyl, cycloalkyl, cycloalkylalkyl, dialkylaminoalkyl, dialkyl-2-oxazolyl, 2-thiazolinyl, 2-benzothiazolyl, 4-phenyl-2-thiazolyl, alkyl-1,3,4-thiadiazolyl, haloalkyl-1,3,4-thiadiazolyl, pyridinyl, halopyridinyl, phenyl, halophenyl, halophenylalkyl, haloalkoxyphenyl, or dialkyl-2,3-dihydrobenzofuran-7-yl;
provided that:
when X is S, Y is $R^3R^2N$,
when X is $R^1N$, Y is RS, $R^1$ is other than alkyl and R is other than haloalkenyl; and
when X is $R^1N$ where $R^1$ is CN and Y is RS, R is other than alkali metal.

The compounds exhibit nematicidal and anthelmintic activity and are useful in agriculture and veterinary practice.

22 Claims, No Drawings

S-TRIFLUOROBUTENYL DERIVATIVES AND PESTICIDAL USES THEREOF

TECHNICAL FIELD

This invention relates to biocidally active S-trifluorobutenyl derivatives and their use, principally in agriculture and veterinary practice, for combatting nematodes and helminths, and diseases induced by such pests.

Representative of research efforts in the field are the compounds disclosed in U.S. Pat. Nos. 3,510,503 to Brokke et al. and 3,658,901 to Timmons et al. U.S. Pat. Nos. 3,654,333, 3,654,362 and 3,689,662 are based on U.S. Pat. No. 3,510,503.

SUMMARY OF THE INVENTION

The compounds of the invention are S-trifluorobutenyl thiocarbonic acid esters of the formula (I):

and salts thereof,
wherein X is $R^1N$ or S and Y is RS or $R^3R^2N$;
wherein R is a metal or a radical selected from alkyl, cycloalkylalkyl, halocycloalkylalkyl, alkenyl, haloalkyl, haloalkenyl, alkynyl, alkoxyalkyl, alkylthioalkyl, alkoxycarbonylalkyl, halophenoxyalkyl, trialkylsilylalkyl, (vinyl)dialkylsilylalkyl, (allyl)dialkylsilylalkyl, 2-chlorothiophene-5-ylmethyl, phenylalkyl, halophenylalkyl, nitrophenylalkyl, haloalkylphenylalkyl, dialkyl-2,3-dihydrobenzofuran-7-yl, [2-methyl-(1,1'-biphenyl)-3-yl]methyl, 3-phenoxybenzyl, phenylthioalkyl, halophenylthioalkyl, dialkylphosphoryl, dialkylthiophosphoryl, dialkylisoxazolylalkyl and thienylisoxazolylalkyl;
wherein $R^1$ is alkyl, cycloalkyl, cyano, dialkyl-2,3-dihydrobenzofuran-7-yl, halophenyl, halophenylalkyl, haloalkoxyphenyl, pyridinyl, halopyridinyl, alkyl-1,3,4-thiadiazolyl, haloalkyl-1,3,4-thiadiazolyl, benzothiazolyl, dialkyloxazolyl or thiazolinyl;
wherein $R^2$ is hydrogen or alkyl; and
wherein $R^3$ is alkyl, haloalkyl, cycloalkyl, cycloalkylalkyl, dialkylaminoalkyl, dialkyl-2-oxazolyl, 2-thiazolinyl, 2-benzothiazolyl, 4-phenyl-2-thiazolyl, alkyl-1,3,4-thiadiazolyl, haloalkyl-1,3,4-thiadiazolyl, pyridinyl, halopyridinyl, phenyl, halophenyl, halophenylalkyl, haloalkoxyphenyl, or dialkyl-2,3-dihydrobenzofuran-7-yl;
provided that:
when X is S, Y is $R^3R^2N$,
when X is $R^1N$, Y is RS, $R^1$ is other than alkyl and R is other than haloalkenyl; and
when X is $R^1N$ where $R^1$ is CN and Y is RS, R is other than alkali metal.

The compounds exhibit pesticidal activity against helminths that feed upon plants and against other helminths that are indicators of animal anthelmintic activity. Accordingly, the compounds are useful as nematicides and anthelmintics for both agricultural and veterinary applications.

DETAILED DESCRIPTION

In formula I above, when X is S and Y is $R^3R^2N$, the compounds are dithiocarbamates; and when X is $R^1N$ and Y is RS, the compounds are imidodithiocarbonates, although the compounds may be designated generically as S-trifluorobutenyl thiocarbonic acid esters, differing in the X and Y functionality.

In the definitions of X and Y, halo includes fluoro, chloro, bromo or iodo and can be present as single halogen atoms or as a plurality of halogens, including the same or mixed halogens. Preferably the halogen is fluorine, less preferably chlorine or a mixture of fluorine and chlorine. Typically, alkyl and alkoxy include both straight chain and branched groups containing 1 to about 12 or more carbon atoms. Preferably these groups contain 1–8 carbon atoms, more preferably 1–4 carbon atoms, and when substituted with halogen, preferably are multiply substituted, e.g., trifluoromethyl and trifluoromethoxy. Cycloalkyl typically contains 3 to about 8 carbon atoms. Alkenyl and alkynyl may contain 2 to about 12 or more carbon atoms, preferably 3 to 8, and when halogen-substituted, preferably are multiply substituted, e.g., 3,4,4-trifluoro-3-butenyl and 3,3-dichloro-2-propenyl. Substituted silylalkyl includes [dialkyl(vinyl)silyl]alkyl, [dialkyl(phenyl)silyl]alkyl and [dialkoxy(alkyl)silyl]alkyl.

Metals defining R include agriculturally acceptable monovalent and polyvalent metals such as the alkali metals, e.g., sodium and potassium, and the alkaline earth metals, e.g., magnesium and calcium. Other metals can also be present provided the compounds remain acceptable for agricultural and/or veterinary use.

In some cases the compounds of formula I can form salts and such salts are within the scope of the invention. For example, the dithiocarbamates form metal salts wherein the metal is an alkali, alkaline earth or other metal, e.g., sodium, potassium, and others.

The preferred dithiocarbamates of formula I in terms of nematicidal activity presently appear to be those wherein $R^2$ is hydrogen and $R^3$ is haloalkoxyphenyl, halophenyl or halophenylalkyl; $R^2$ is hydrogen and $R^3$ is a heterocycle; $R^2$ is alkyl and $R^3$ is phenyl or halophenyl; or $R^2$ is alkyl and $R^3$ is a heterocycle. Of the imidodithiocarbonates of formula I, the preferred compounds as nematicides appear at present to be those wherein $R^1$ is cyano and R is alkyl, cycloalkylalkyl, alkenyl, haloalkenyl or dialkylphosphoryl.

The compounds of formula I are prepared in a generally known manner from commercially available reagents. Thus, cyanoimidodithiocarbonates are synthesized by reacting cyanamide with carbon disulfide and potassium hydroxide in ethanol to yield dipotassium cyanoimidodithiocarbonate. The dipotassium salt is then reacted with 4-bromo-1,1,2-trifluoro-1-butene in acetone and water to yield potassium (3,4,4-trifluoro-3-butenyl)cyanoimidodithiocarbonate. The prepared mono-potassium cyanoimidodithiocarbonate is then used in the synthesis of the majority of the product cyanoimidodithiocarbonates by reaction with the appropriate halogenated compound (e.g. methyl iodide, 2,6-difluorobenzyl bromide, etc.) in acetone and water to yield the corresponding product. The synthesis of diethyl phosphate and diethyl thiophosphate derivatives is accomplished by using the appropriate chlorinated phosphate and reacting it with the potassium (3,4,4-trifluoro-3-butenyl)cyanoimidodithiocarbonate intermediate in either methyl ethyl ketone or methyl ethyl ketone with 1,4,7,10,13,16-hexaoxacyclooctadecane (18-crown-6) to yield the appropriate product.

The imidodithiocarbonates, such as methyl (3,4,4-trifluoro-3-butenyl) N-(methyl)imidodithiocarbonate, are synthesized by reacting methylamine hydrochloride with carbon disulfide and potassium hydroxide in ethanol to yield the dipotassium salt. The dipotassium salt is then reacted with 4-bromo-1,1,2-trifluoro-1-butene in acetone, followed by treatment with dilute hydrochloric acid in diethyl ether to yield (3,4,4-trifluoro-3-butenyl) N-(methyl)dithiocarbamate. The ester in turn is reacted with methyl iodide in acetone with potassium carbonate as the acid acceptor to yield the appropriate product.

Similarly, other dithiocarbamates and imidodithiocarbonates are synthesized by reacting the appropriate amine intermediate with carbon disulfide and sodium hydroxide in dimethyl sulfoxide, and then in-situ with 4-bromo-1,1,2-trifluoro-1-butene, to yield the corresponding dithiocarbamate. The dithiocarbamate is then alkylated with the appropriate halogenated reactant (e.g. methyl iodide, (bromomethyl)cyclopropane, etc.) and either sodium hydroxide or triethylamine as the acid acceptor in dimethylformamide to yield the corresponding imidodithiocarbonate. When the starting amine is 2-amino-5-methyl-1,3,4-thiadiazole or 2-amino-5-trifluoromethyl-1,3,4-thiadiazole, synthesis proceeds as in the same manner except that when alkylating with methyl iodide two products are obtained and separated. The two products are the result of methylation on either the sulfur or the nitrogen.

Intermediates are prepared as needed. For example, 2-amino-4,5-dimethyl-2-oxazole is prepared by reacting cyanamide with acetyl methyl carbinol in water and heating at 40°-50° C. Once the amine is obtained, the sequence of reactions is the same as described immediately above.

Further details of synthesis are given in the representative examples below. Table 1 (appended) lists the compounds of the examples and other compounds of formula I together with root-knot nematicidal activity. Subsequent tables provide information on other biological activity. In Table 1, the compound numbers not also designated with a letter are representative of the imidodithiocarbonates of the invention. In the synthesis examples and the activity evaluations following, all parts and percentages are by weight unless otherwise indicated.

EXAMPLE 1

Potassium (3,4,4-trifluoro-3-butenyl)cyanoimidodithiocarbonate (Compound 1)

(a) Carbon disulfide (105 grams, 1.38 mole) was added to a stirred solution of cyanamide (53.0 grams, 1.25 mole) in absolute ethanol (100 ml) under a nitrogen atmosphere. After cooling the reaction mixture to 0° C., a solution of potassium hydroxide (140.5 grams, 2.5 mole) in absolute ethanol (450 ml) was added dropwise. During the addition the reaction mixture temperature was kept below 10° C. The reaction mixture was then stirred overnight at ambient temperature. The solid that had formed was removed by filtration, washed with ethanol, and dried in a vacuum oven, yielding 147.88 grams of dipotassium cyanoimidodithiocarbonate. The NMR spectrum was consistent with the proposed structure.

(b) A solution of 4-bromo-1,1,2-trifluoro-1-butene in acetone (10 ml) was added to a stirred solution of dipotassium cyanoimidodithiocarbonate (5.0 grams, 0.026 mole) in acetone (19 ml) and water (22 ml) that had been cooled to 0° C. Upon completion of addition, the reaction mixture was stirred at ambient temperature overnight. The reaction mixture was concentrated under reduced pressure and dried in a vacuum oven, yielding potassium (3,4,4-trifluoro-3-butenyl)cyanoimidodithiocarbonate. This product was used in the preparation of Compounds 1–29 and 49–81 (Table 1).

EXAMPLE 2

Cyclopropylmethyl (3,4,4-trifluoro-3-butenyl)cyanoimidodithiocarbonate (Compound 9)

A solution of bromomethylcyclopropane (0.6 gram, 0.004 mole) in acetone (4 ml) was added to a stirred solution of potassium (3,4,4-trifluoro-3-butenyl)-cyanoimidodithiocarbonate (1.0 gram, 0.0038 mole) in water (5 ml) and acetone (4 ml) that had been cooled to 0° C. The reaction mixture was then stirred at ambient temperature overnight. After the reaction mixture had been concentrated under reduced pressure, the residue was dissolved in acetone and filtered. The filtrate was concentrated under reduced pressure leaving a residue. This residue was passed through a column of silica gel, eluting with diethyl ether. Appropriate fractions were combined and concentrated under reduced pressure, yielding 0.78 gram of cyclopropylmethyl(3,4,4-trifluoro-3-butenyl)cyanoimidodithiocarbonate. The NMR spectrum was consistent with the proposed structure.

Compounds 2–6, 8, 10, 12–15, 17–22, 24, 26, 49, 77, 78 and 80 (Table 1) were made in a manner similar to Example 2. In the synthesis of Compounds 7, 56, 59, 70 and 76, the acetone or acetone/water combination was replaced with tetrahydrofuran. Similarly, Compounds 50, 51 and 66 were made using methanol as solvent; Compounds 11, 72 and 73 were made using dimethylformamide as solvent; and Compounds 27, 52–56, 58, 60–65, 67–69, 71, 74, 75, 79 and 81 were made using dimethylsulfoxide as solvent.

EXAMPLE 3

(3,3-Dibromo-2-propenyl) (3,4,4-trifluoro-3-butenyl) cyanoimidodithiocarbonate (Compound 16)

(a) A mixture of 1,1-dibromopropene (10.0 grams, 0.05 mole) and N-bromosuccinimide (8.9 grams, 0.05 mole) in carbon tetrachloride (75 ml) was irradiated with a sun lamp for three hours. Upon cooling, the solid was removed by filtration, and the filtrate was concentrated under reduced pressure. The residue was distilled using a Kugelrohr apparatus to yield 4.0 grams of 1,1,3-tribromo-1-propene as a colorless oil. The NMR spectrum was consistent with the proposed structure. The intermediate, 1,1-dichloro-3-bromo-1-propene, was synthesized in the same manner from 1,1-dichloropropene and N-bromosuccinimide.

(b) A solution of 1,1,3-tribromo-1-propene (2.16 grams, 0.005 mole) in dimethyl sulfoxide (4 ml) was added to a stirred solution of potassium (3,4,4-trifluoro-3-butenyl)cyanoimidodithiocarbonate (1.39 grams, 0.005 mole) in dimethyl sulfoxide (9 ml). The reaction mixture was stirred overnight at ambient temperature. The reaction mixture was diluted with diethyl ether (200 ml) and washed with water (5×50 ml). The dried (magnesium sulfate) organic layer was concentrated under reduced pressure leaving a residue. This residue was passed through a column of silica gel, eluting with 1:1 diethyl ether:hexane. Appropriate fractions were combined and concentrated under reduced pressure, yielding 1.40 grams of (3,3-dibromo-2-propenyl) (3,4,4-trifluoro-3-butenyl)cyanoimidodithiocarbonate, as a yellow oil. The NMR spectrum was consistent with the proposed structure.

EXAMPLE 4

(2,2-Dimethyl-2,3-dihydrobenzofuran-7-ylmethyl) (3,4,4-trifluoro-3-butenyl)cyanoimidodithiocarbonate) (Compound 23)

(a) n-Butyl lithium, 2.7M, (25.04 ml, 0.0676 mole) was added to a stirred solution of 2,3-dihydro-2,2-dimethylbenzofuran (10.0 grams, 0.0676 mole) in tetrahydrofuran (75 ml) at −78° C. The reaction mixture was then stirred at 0° C. for two hours after which it was added to a cooled (−78° C.) solution of dimethylformamide (5.42 ml, 0.07 mole) in tetrahydrofuran (25 ml). Upon completion of addition, the reaction mixture was stirred at −78° C. for ten minutes and then warmed to ambient temperature. The reaction mixture was quenched with aqueous ammonium chloride (1M, 150 ml) and stirred for three hours at ambient temperature. The reaction mixture was extracted with diethyl ether (2×150 ml), and the combined extract was washed with a saturated aqueous solution of sodium chloride. The dried (magnesium sulfate) extract was concentrated under reduced pressure leaving a residue. This residue was distilled, yielding 3.72 grams of 2,3-dihydro-2,2-dimethylbenzofuran-7-carboxaldehyde, b.p. 80°-83° C./0.2 mmHg. The NMR spectrum was consistent with the proposed structure.

(b) Sodium borohydride (1.08 grams, 0.0285 mole) was added carefully in small portions to a stirred solution of 2,3-dihydro-2,2-dimethylbenzofuran-7-carboxaldehyde (10.0 grams, 0.057 mole) in ethanol (150 ml) at 5°-10° C. during a ten minute period. The reaction mixture was stirred for thirty minutes and was then quenched by the dropwise addition of water (25 ml) followed by 10% hydrochloric acid (25 ml). The reaction mixture was concentrated under reduced pressure leaving a residue. This residue was partitioned between diethyl ether (75 ml) and 10% hydrochloric acid (30 ml). The layers were separated, and the organic layer was washed with water (40 ml) and a saturated aqueous solution of sodium chloride (40 ml). The dried (sodium sulfate) organic solution was concentrated under reduced pressure, yielding 2,3-dihydro-2,2-dimethylbenzofuran-7-ylmethanol as a solid. The NMR spectrum was consistent with the proposed structure.

(c) A mixture of 2,3-dihydro-2,2-dimethylbenzofuran-7-ylmethanol (6.3 grams, 0.035 mole) and concentrated hydrochloric acid (38%) was stirred at ambient temperature for 0.75 hour. The reaction mixture was diluted with water (50 ml) and extracted with diethyl ether. The extract was washed successively with a 10% aqueous solution of sodium hydroxide and a saturated aqueous sodium chloride solution. The dried (sodium sulfate) extract was concentrated under reduced pressure, yielding 7-chloromethyl-2,3-dihydro-2,2-dimethyl-benzofuran. The NMR spectrum was consistent with the proposed structure.

(d) In a manner similar to Example 2, potassium(3,4,4-trifluoro-3-butenyl)cyanoimidodithiocarbonate (1.0 gram, 0.0038 mole) and 7-chloromethyl-2,3-dihydro-2,2-dimethylbenzofuran were reacted to produce (2,2-dimethyl-2,3-dihydrobenzofuran-7-ylmethyl)(3,4,4-trifluoro-3-butenyl)cyanoimidodithiocarbonate. The NMR spectrum was consistent with the proposed structure.

EXAMPLE 5

3-Phenoxybenzyl(3,4,4-trifluoro-3-butenyl)cyanoimidocarbonate (Compound 25)

(a) A solution of 3-phenoxybenzyl alcohol (36.0 grams, 0.18 mole) in toluene (95 ml) was added dropwise during a thirty minute period to a stirred solution of thionyl bromide (50 grams, 0.24 mole), pyridine (0.5 gram) and toluene (175 ml) while maintaining the temperature below 30° C. After the addition was complete, the reaction mixture was heated at 50°-60° C. for two hours. Upon cooling, the reaction mixture was concentrated under reduced pressure leaving a residue. This residue was dissolved in toluene (200 ml) and washed with water (10×100 ml) until a neutral pH was obtained. The dried (magnesium sulfate) toluene layer was concentrated under reduced pressure leaving a residue. This residue was distilled yielding 38.5 grams of 3-phenoxybenzyl bromide, b.p. 120°-144° C./0.05 mmHg. The NMR spectrum was consistent with the proposed structure.

(b) In a manner similar to Example 2, potassium(3,4,4-trifluoro-3-butenyl)cyanoimidodithiocarbonate (1.0 gram, 0.0038 mole) and 3-phenoxybenzyl bromide (1.0 gram, 0.0038 mole) were reacted, producing 3-phenoxybenzyl(3,4,4-trifluoro-3-butenyl)cyanoimidodithiocarbonate. The NMR spectrum was consistent with the proposed structure.

EXAMPLE 6

(3,4,4-Trifluoro-3-butenyl)cyanoimidodithiocarbonic acid anhydride with diethyl phosphoric acid (Compound 28)

To a stirred solution of potassium(3,4,4-trifluoro-3-butenyl)cyanoimidodithiocarbonate (3.0 grams, 0.0113 mole) in methyl ethyl ketone (24 ml) was added diethyl chlorophosphate (1.96 grams, 0.0113 mole) under a nitrogen atmosphere. The reaction mixture was allowed to stir at ambient temperature under nitrogen for two days. The reaction mixture was concentrated under reduced pressure leaving a residue. This residue was redissolved in toluene (50 ml) and washed successively with water (25 ml), a 5% aqueous solution of sodium hydroxide (2×25 ml), water (25 ml), and a saturated aqueous sodium chloride solution (25 ml). The dried (magnesium sulfate) organic layer was concentrated under reduced pressure leaving a residue. This residue was passed through a silica gel column, eluting first with hexane and finally with hexane:ethyl acetate (7:3). Appropriate fractions were combined and concentrated under reduced pressure, yielding 1.15 grams of (3,4,4-trifluoro-3-butenyl)cyanoimidodithiocarbonic acid anhydride with diethyl phosphoric acid as an orange oil. The NRM spectrum was consistent with the proposed structure.

EXAMPLE 7

(3,4,4-Trifluoro-3-butenyl)cyanoimidodithiocarbonic acid anhydride with O,O-diethyl thiophosphoric acid (Compound 29)

Diethyl chlorothiophosphate (1.88 grams, 0.01 mole) was added to a stirred solution of potassium(3,4,4-trifluoro-3-butenyl)cyanoimidodithiocarbonate (2.64 grams, 0.01 mole) in butanone (35 ml ) at ambient temperature. Upon completion of addition, a small amount of 1,4,7,10,13,16-hexaoxacyclooctadecane was added. The reaction mixture was stirred overnight at ambient temperature, and then refluxed for two hours. The reaction mixture was concentrated under reduced pressure leaving a residue. This residue was dissolved in diethyl ether and washed successively with a 5% aqueous solution of sodium hydroxide (5 ml) and water (5 ml). The dried (sodium sulfate) organic layer was concentrated under reduced pressure, yielding (3,4,4-trifluoro-3-butenyl)cyanoimidodithiocarbonic acid anhydride with O,O-diethyl thiophosphoric acid. The NMR spectrum was consistent with the proposed structure.

EXAMPLE 8

Methyl(3,4,4-trifluoro-3-butenyl) N-(methyl)imidodithiocarbonate (Compound 30)

(a) Aqueous potassium hydroxide (3.0 g×85%, 0.045 mole) was added dropwise to a stirred mixture of methylamine hydrochloride (3.0 grams, 0.045 mole) in 60 ml of 95% ethanol at −10° C. Following this addition, carbon disulfide was added dropwise at −10° C. Upon completion of addition, a solution of potassium hydroxide (6.0 grams, 0.09 mole) in 95% ethanol was added dropwise. The reaction mixture was allowed to stir overnight at ambient temperature. The precipitate which had formed was collected by filtration, washed with diethyl ether, and dried under high vacuum, yielding dipotassium N-(methyl)imidodithiocarbonate. The NMR spectrum was consistent with the proposed structure.

(b) A mixture of dipotassium N-(methyl)imidodithiocarbonate (3.1 grams, 0.017 mole) and 4-bromo-1,1,2-trifluoro-1-butene (2.9 grams, 0.017 mole) in acetone (50 ml) was stirred overnight at ambient temperature. The reaction mixture was then heated at reflux for 2.5 hours. Upon cooling, the reaction mixture was concentrated under reduced pressure leaving a residue. This residue was diluted with diethyl ether, a dilute hydrochloric acid was added. The reaction mixture was shaken, the layers separated, and the organic layer was dried (magnesium sulfate). The organic solution was concentrated under reduced pressure, yielding (3,4,4-trifluoro-3-butenyl) N-(methyl)dithiocarbamate. The NMR spectrum was consistent with the proposed structure.

(c) (3,4,4-Trifluoro-3-butenyl) N-(methyl)dithiocarbamate (1.5 grams, 0.097 mole), methyl iodide (1.5 grams, 0.01 mole), and potassium carbonate (1.0 gram, 0.007 mole) in acetone (30 ml) were stirred at ambient temperature for three days. The reaction mixture was concentrated under reduced pressure, leaving a residue. This residue was dissolved in diethyl ether, forming a precipitate which was removed by filtration. The filtrate was washed with a 2% aqueous solution of sodium hydroxide (2×), dried (magnesium sulfate), and concentrated under reduced pressure, yielding methyl(3,4,4-trifluoro-3-butenyl) N-(methyl)imidodithiocarbonate as an orange liquid. The NMR spectrum was consistent with the proposed structure.

EXAMPLE 9

Methyl(3,4,4-trifluoro-3-butenyl) N-(2,3-dihydro-2,2-dimethylbenzofuran-7-yl)imidodithiocarbonate (Compound 31)

(a) Sodium hydroxide (3.7 ml, 20M) was added to a stirred solution of 7-amino-2,3-dihydro-2,2-dimethylbenzofuran (10 grams, 0.061 mole) in dimethyl sulfoxide (31 ml). Upon completion of addition, carbon disulfide (6.06 grams, 0.08 mole) was added. The reaction mixture was stirred for one hour at ambient temperature, then cooled to 0° C. at which time 4-bromo-1,1,2-trifluoro-1-butene was added dropwise. The reaction mixture was stirred at ambient temperature overnight. The reaction mixture was diluted with water (400 ml) and extracted with diethyl ether. The extract was dried (sodium sulfate) and concentrated under reduced pressure leaving a residue. This residue was passed through a column of silica gel, eluting with hexane:diethyl ether (9:1). Appropriate fractions were combined and concentrated under reduced pressure, yielding (3,4,4-trifluoro-3-butenyl) N-(2,3-dihydro-2,2-dimethylbenzofuran-7-yl)dithiocarbamate (Compound A12). The NMR spectrum was consistent with the proposed structure.

Compounds A1, A3–A11, A13, A14 and A17–A27 were synthesized in a similar manner.

(b) Sodium hydroxide (0.3 ml of 20M) was added to a stirred solution of (3,4,4-trifluoro-3-butenyl) N-(2,3-dihydro-2,2-dimethylbenzofuran-7-yl)dithiocarbamate (1.5 grams, 0.043 mole) in dimethyl formamide (5 ml). The reaction mixture was stirred for one hour at ambient temperature, then cooled to 0° C. at which time methyl iodide (0.27 ml, 0.0043 mole) was added. The reaction mixture was stirred at ambient temperature overnight, after which it was diluted with water (100 ml) and extracted with diethyl ether (2×). The combined extracts were concentrated under reduced pressure leaving a residue. This residue was passed through a column of silica gel, eluting with hexane:diethyl ether (9:1). Appropriate fractions were combined and concentrated under reduced pressure, yielding methyl(3,4,4-trifluoro-3-butenyl) N-(2,3-dihydro-2,2-dimethylbenzofuran-7-yl)imidodithiocarbonate. The NMR spectrum was consistent with the proposed structure.

Compounds 33, 38–40, 43–48 and 82–105 (Table 1) were synthesized in a similar manner. Compounds 32, 34, 35, 41 and 42 (Table 1) were synthesized in a similar manner using triethylamine in dimethylformamide instead of sodium hydroxide. Compounds 106 and 107 (Table 1) were synthesized in a similar manner using triethylamine in dimethylsulfoxide instead of sodium hydroxide.

EXAMPLE 10

Methyl(3,4,4-trifluoro-3-butenyl) N-(5-trifluoromethyl-1,3,4-thiadiazol-2-yl)imidodithiocarbonate (Compound 37) and (3,4,4-Trifluoro-3-butenyl) N-(methyl)-N-(5-trifluoromethyl-1,3,4-thiadiazol-2-yl)-dithiocarbamate (Compound A16)

(a) Carbon disulfide (5.78 grams, 0.076 mole) was added to a stirred solution of 2-amino-5-trifluoromethyl-1,3,4-thiadiazole (12.0 grams, 0.071 mole) in dimethyl sulfoxide (36 ml) under a nitrogen atmosphere. The reaction mixture was stirred for three hours at ambient temperature, then cooled to 0° C. at which time 4-bromo-1,1,2-trifluoro-1-butene (16.8 grams, 0.088 mole) was added dropwise. The reaction mixture was stirred at ambient temperature overnight. Crystals that had formed were collected by filtration, washed successively with petroleum ether and hexane and then dried, yielding 8.39 grams of (3,4,4-trifluoro-3-butenyl) N-(5-trifluoromethyl-1,3,4-thiadiazol-2-yl)-dithiocarbamate as a yellow powder. The NMR spectrum was consistent with the proposed structure.

(b) Triethylamine (0.69 gram, 0.0068 mole) was added to a stirred solution of (3,4,4-trifluoro-3-butenyl) N-(5-trifluoromethyl-1,3,4-thiadiazol-2-yl)-dithiocarbamate (2.0 grams, 0.0057 mole) in dimethylformamide (5.7 ml) at ambient temperature. After addition was complete, the reaction mixture stirred for one hour and was then cooled to 0° C. Methyl iodide (1.0 gram, 0.0063 mole) was added to the cooled mixture. After warming to ambient temperature, the reaction mixture was stirred overnight. The reaction mixture was diluted with water (200 ml) and extracted three times with diethyl ether. The combined extracts were washed with 10% aqueous hydrochloric acid. The dried (magnesium sulfate) extracts were concentrated under reduced pressure, leaving a residue. This residue was passed through a column of silica gel, eluting with hexane to yield the first product (3,4,4-trifluoro-3-butenyl) N-(methyl)-N-(5-trifluoromethyl-1,3,4-thiadiazol-2-yl)dithiocarbamate (0.45 gram) as a yellow oil. Eluting solvent was then changed to hexane:ethyl acetate (1:1) to yield the second product methyl(3,4,4-trifluoro-3-butenyl) N-(5-trifluoromethyl-1,3,4-thiadiazol-2-yl)imidodithiocarbonate (0.96 gram) as an orange oil. The NMR spectra were consistent with the proposed structures.

Compounds 36 and A15 (Table 1) were prepared in a similar manner.

EXAMPLE 11

(3,4,4-Trifluoro-3-butenyl) N-(4,5-dimethyl-2-oxazolyl)dithiocarbamate (Compound A2)

(a) A mixture of cyanamide (21.0 grams, 0.5 mole) and acetyl methyl carbinol (51.82 grams×85%, 0.5 mole) in water (65 ml) was heated to 40°–50° C. After three minutes the reaction mixture was cooled to 20° C., and the pH was adjusted to pH 10 with a 10% aqueous solution of sodium hydroxide. This mixture was extracted with diethyl ether (5×80 ml). The combined extracts were dried and concentrated under reduced pressure, yielding 2-amino-4,5-dimethyloxazole.

(b) In a manner similar to Example 9, Step (a), 2-amino-4,5-dimethyloxazole (3.0 grams, 0.027 mole), carbon disulfide (2.67 grams, 0.035 mole), triethylamine (3.44 grams, 0.34 mole), dimethyl sulfoxide (13.5 ml) and 4-bromo-1,1,2-trifluoro-1-butene (6.43 grams, 0.034 mole) were reacted to produce 2.78 grams of (3,4,4-trifluoro-3-butenyl) N-(4,5-dimethyl-2-oxazolyl)dithiocarbamate. The NMR spectrum was consistent with the proposed structure.

Pesticidal Use

The compounds of the invention can be used against a variety of pests that attack plants and animals. In agriculture, they are useful as nematicides, particularly against plant-parasitic nematodes and "free-living" nematodes, i.e., nematodes not dependent on any specific plant or other host. An example of the latter is the microbivorous nematode *Caenorhabditis elegans.* This nematode will feed on bacteria such as *Escherichia coli* and is used as a screen for both agricultural and veterinary nematicides or anthelmintics.

When used as anthelmintics, in veterinary treatments for treatment of infestations of *Ascaris lumbricoides* (roundworm in pigs) for example, the compounds may be administered orally, parenterally or topically either alone but more usually in a pharmaceutically acceptable carrier, to provide an appropriate dosage. Such carriers include one or more of water, gelatine, sugars, starches, organic acids such as stearic or citric acid and salts thereof, talc, vegetable fats or oils, gums, glycols and other excipients, for administration as solids (e.g., tablets or capsules) or liquids (e.g., solutions, suspensions or emulsions). The compositions may also contain preservatives, stabilizers, wetting or emulsifying agents, buffers, salts and other therapeutic agents. The compositions may be formulated by conventional methods to contain about 5 to 95% by weight of the anthelmintic compound, preferably about 25 to 75% by weight. Further guidance to anthelmintic activity, formulations and modes of treatment, utilizing the compounds of the invention, is available from publications on the subject, such as the article "Chemotherapeutics, Anthelmintic" in Kirk-Othmer, Encyclopedia of Chemical Technology, Third ed., 5, 451–468, and articles cited therein, and in the patent literature, such as U.S. Pat. No. 3,576,892, col. 3, lines 29–56.

As agricultural pesticides, the nematicides of this invention may be applied neat to infestations or to the locus where infestations may occurs. However, like most agricultural chemicals, they are more usually not applied full strength, but are formulated with agriculturally acceptable carriers normally employed for facilitating the dispersion of active ingredients, with various additives, and optionally with other active ingredients, recognizing the accepted fact that the formulation and mode of application of a toxicant may affect the activity of the material. The present compounds may be applied, for example, to the soil in which nematode or soil insect control is desired, as granules or powders or liquids, the choice of application varying, of course, with the nematode or soil insect species and environmental factors present at the particular locus of infestation. Thus, the compounds may be formulated as granules of various sizes, as dusts, as wettable powders, as emulsifiable concentrates, as solutions, as dispersions, as controlled release compositions, and the like.

A typical formulation may vary widely in concentration of the active ingredient depending on the particular agent used, the additives and carriers used, other active ingredients, and the desired mode of application. With due consideration of these factors, the active ingredient of a typical formulation may, for example, be suitably present at a concentration of from about 0.5% up to about 99.5% by weight of the formulation. Substantially inactive ingredients such as adjuvants and carriers may comprise from about 99.5% by weight to as low as about 0.5% by weight of the formulation. Surface active agents, if employed in the formulation, may be present at various concentrations, suitably in the range of 1 to 30% by weight. The following description, along with the typical formulations used for the biological testing, will serve to guide the formulator in preparing the most effective formulations. In this specification, "carrier" is intended to mean and include diluents, extenders and other vehicles commonly employed in pesticidal and veterinary formulations to control application rates and dosages.

Dusts are admixtures of the active ingredient with finely divided solid carriers and/or diluents such as talc, natural clays, kieselguhr, pyrophyllite, chalk, diatomaceous earths, calcium phosphates, calcium and magnesium carbonates, sulfur, lime, flours, and other organic and inorganic solid carriers. These finely divided formulations generally have an average particle size of less than about 45 $\mu$m, (No. 325, U.S.A. Standard Sieve Series). In most cases, the active ingredient will be present in dust formulations at a concentration in the range of 1 to 15%, and occasionally from 1% to about 30%, the balance of the composition typically being agriculturally acceptable carrier or diluent.

Wettable powders, also useful formulations for these biocides, are in the form of finely divided particles which disperse readily in water or other liquid vehicles. The wettable powder is utimately applied to the soil or plant as a dry dust or a dispersion in water or other liquid. Typical carriers for wettable powders include fuller's earth, kaolin clays, silicas, and other highly absorbent or adsorbent inorganic diluents. The concentration of active ingredient in wettable powders is dependent upon physical properties of the active ingredient and the absorbency characteristics of the carrier. Liquids and low melting solids (mp <100° C.) are suitably formulated in the concentration range of 5 to 50% by weight, usually from 10 to 30%; high melting solids (mp <100° C.) are formulated in the range of 5 to 95% by weight, usually 50 to 85%. An agriculturally acceptable carrier or diluent, frequently including a small amount of a surfactant to facilitate wetting, dispersion, and suspension, accounts for the balance of the formulation.

Granules are admixtures of the active ingredients with solids of particle sizes generally in the range of 4.75 mm to 150 μm (No. 4 to No. 100, U.S.A. Standard Sieve Series). Granular formulations may employ hard core materials such as sands and other silicates, mineral carbonates, sulfates or phosphates and the like, or porous cores such as attapulgite clays, fuller's earth, kieselguhr, chalk, diatomaceous earths, ground corn cobs, wood dusts and the like. Impregnating or binding agents such as aliphatic and aromatic petroleum solvents, alcohols, ethers, ketones, esters, vegetable oils, polyvinyl acetates, polyvinyl alcohols, dextrins, sugars and the like are commonly used to aid in coating or impregnating the solid carriers with the active ingredient. Emulsifying agents, wetting agents, dispersing agents, and other additives known in the art may also be added.

A typical granular formulation may suitably contain from about 1% to about 50% by weight active ingredient and 99% to 50% by weight of inert materials.

Microencapsulated or other controlled release formulations may also be used with biocides of this invention.

Emulsifiable concentrates (EC's) are homogeneous liquid compositions, usually containing the active ingredient dissolved in a liquid carrier. Commonly used liquid carriers include xylene, heavy aromatic naphthas, isophorone, and other nonvolatile or slightly volatile organic solvents. For application of the active ingredient, these concentrates are dispersed in water, or other liquid vehicle, forming an emulsion, and are normally applied as a spray to the area to be treated. The concentration of the essential active ingredient in EC's may vary according to the manner in which the composition is to be applied, but, in general, is in the range of 0.5 to 95%, frequently 10 to 80%, by weight of active ingredient, with the remaining 99.5 to 5% being surfactant and liquid carrier.

Those compounds of the invention which are solids (most are liquids) may be formulated as flowable compositions. Flowables are similar to EC's except that the solid active ingredient is suspended in a liquid carrier, generally water. Flowables, like EC's may include a small amount of a surfactant, and contain solid active ingredient in the range of 0.5 to 95%, frequently from 10 to 50%, by weight of the composition. For application, flowables may be diluted in water or other liquid vehicle, and are normally applied as a spray to the area to be treated.

Typical wetting, dispersing or emulsifying agents used in nematicidal formulations include, but are not limited to, the alkyl and alkylaryl sulfonates and sulfates and their sodium salts; alkylamide sulfonates, including fatty methyl taurides; alkylaryl polyether alcohols, sulfated higher alcohols; polyethylene oxides; sulfated animal and vegetable oils; sulfonated petroleum oils; fatty acid esters of polyhydric alcohols and the ethylene oxide addition products of such ester; and the addition product of long-chain mercaptans and ethylene oxide. Many other types of useful surface-active agents are available in commerce. The surface-active agent, when used, normally comprises about 1 to 15% by weight of the biocidal composition.

Other useful formulations include simple solutions of the active ingredient in a relatively nonvolatile solvent such as corn oil, kerosene, propylene glycol, an alcohol, a ketone or other organic solvent. This type of formulation is particularly useful for ultra low volume application.

The concentration of the biocide in use dilution is normally in the range of about 2% to about 0.1%. Many variations of spraying, dusting, soil-incorporated, and controlled or slow release compositions in the art may be used by substituting or adding a compound of this invention into compositions known or apparent to the art.

Pesticidal compositions of the present invention may be formulated and applied with other suitable active ingredients, including other nematicides, insecticides, acaricides, fungicides, plant regulators, herbicides, fertilizers, or with synergists.

In applying the compounds of the invention, whether alone or with other agricultural chemicals, an effective biocidal amount must be used. While the application rate will vary widely depending on the choice of compound, the formulation and mode of application, the plant species being protected, the planting density and the pest pressure, a suitable use rate may be in the range of 0.5 to 25 kg/hectare, preferably 1 to about 20 kg/hectare. Trees and vines, for example, may require at least 5 kg/hectare whereas annuals such as corn may require considerably lower rates of application, for example 1 to 5 kg/hectare. The compounds of the invention are, for the most part, liquids at ambient temperatures and pressures, and therefore can be applied as contact or fumigant pesticides to control soil-borne nematodes.

Illustrative formulations for applying the compounds of the invention include the following:

|  | % (wt/wt) |
|---|---|
| Typical suspension | |
| Test Compound | 0.2 |
| Dimethylsulfoxide | 99.8 |
| Typical solution | |
| Test Compound | 0.3 |
| Acetone | 55.9 |
| Water | 43.8 |
| Typical 5% dust | |
| Test Compound | 5 |
| Base | 95 |
| 96% attaclay | |
| 2% highly purified sodium | |

-continued

| | % (wt/wt) |
|---|---|
| lignosulfonate (100%) | |
| 2% powdered sodium alkyl- naphthalene sulfonate (75%) | |
| Typical 5% emulsifiable concentrate | |
| Test Compound | 5.0 |
| Emulsifier A | 4.0 |
| Emulsifier B | 0.4 |
| Emulsifier C | 0.8 |
| Emulsifier D | 1.3 |
| Refined xylene solvent | 88.5 |

Emulsifier A is the anionic calcium salt of dodecylbenzene sulfonate. Emulsifier B is a nonionic 6-molar ethylene oxide condensation product with nonylphenol. Emulsifier C is a nonionic 30-molar ethylene oxide condensation product with nonylphenol. Emulsifier D is a nonionic paste of 100% polyalkylene glycol ether.

| Typical 1% and 5% granular formulations | % (wt/wt) | |
|---|---|---|
| Test Compound | 1 | 5 |
| Attapulgite carrier/diluent | 99 | 95 |

The carrier/diluent is a 20/40 or 60/90 mesh hydrated aluminum magnesium silicate of low volatile matter having 2% free moisture.

Biological Testing

The compounds of the invention were tested against the soil-borne root-knot nematode (*Meloidogyne incognital*), the stunt nematode (*Tylenchorhynchus claytoni*), the lesion nematode (*Pratylenchus penetrans*), the soybean cyst nematode (*Heterodera glycines*), and the free-living *Caenorhabditis elegans* helminth. For these tests (described below), the compounds were formulated as standard dusts or water/acetone solutions as described above.

1. Root-knot Nematode Screening Test

The formulated candidate nematicide was incorporated at rates varying from 10 to 0.078 ppm in soil previously infested with root-knot nematode eggs and larvae. The treated soil was then placed in 7.6 cm fiber pots. A cucumber or a tomato seedling was planted in each pot. The tests were evaluated approximately two-weeks post-treatment. The results for activity at 2.5 ppm application rate are given in Tables 1 and 1a appended where the ratings are as follows:
A+++ = 80-100% control
A++ = 60-80% control
A+ = 30-60% control
A = 0-30% control.
The test results show that compounds 2-5, 8, 9, 11, 12, 16-18, 20, 26-28, A2, A3, A8, A10, A11, A13 and A16 provided 80% or better control of the nematode at an application rate of 2.5 ppm. Compound 9 provided 83% control at 0.312 ppm.

2. C. Elegans Nematode Screening Test and Evaluation

This in-vitro test using the free-living nematode, *Caenorhabditis elegans*, is a modification of the assay developed by Simpkin and Coles, *J. Chem. Tech. Biotechnol*, 31:66-69 (1981). In this test, nematicidal activity is evaluated by placing a suspension of *C. elegans* nematodes in a medium containing a food source (*E. coli*) and a candidate nematicide at test rates of 5.0-0.156 ppm. One milliliter of a test medium consisting of 5 mg ampicillin, 10,000 units of mycostatin and 10 ml of a dense suspension of *Escherichia coli* per 100 ml of a buffer solution, was pipetted into each well of a 24-well microtiter plate. The candidate nematicide, suspended at the appropriate concentration in dimethylsulfoxide, was added to the wells in 2.5 $\mu$l volumes. Each rate of application was replicated two to three times. After thorough mixing of the contents of each well, 50 to 100 $\mu$l of a nematode suspension in a buffer was added so that each well received 10-15 nematodes. After the nematodes were added, the microtiter plates were incubated at 20° C. for 5-6 days.

The effect of the candidate nematicide on the survival and the reproduction of *C. elegans* was then evaluated by comparison of the level of population development in the treated wells with that in untreated wells. Specific effects on population development, such as reduced egg hatch or molting disruption, were noted if they were evident. Tables 2 and 3 appended show test results for some of the compounds of the invention. The most active compound was A14 (100% inhibition of reproduction and 92% mortality at the low application rate of 1.25 ppm). In addition to good inhibition of reproduction and high percent mortality, compound 2 reduced egg hatch.

3. Stunt Nematode

Formulated candidate nematicide was incorporated at rates of 2.5 or 5 ppm in soil. The treated soil was placed in 10.2 cm fiber pots and planted with corn seedlings. All pots were then infested with a combination of larvae and adult stunt nematodes. The tests were evaluated approximately four weeks post-infestation. The results (Table 4 appended) show that compounds 2 and 9 provided the best activity (90% and 85% control, respectively, at 5 ppm).

4. Lesion Nematode

This test was the same as for the stunt nematode except pea seedlings and 7.6 cm fiber pots were used. Table 5 (appended) shows that compounds 3 and 33 exhibited the best activity (70% and 61% control, respectively, at 2.5 ppm).

5. Cyst Nematode

The test was the same as for the stunt nematode except soybean seedlings were used. Table 6 (appended) shows that compound 9 gave 66% control at 5 ppm.

6. Systemic Activity

Tomato plants were grown in 10 cm fiber pots until they had four to six true leaves. Three plants per candidate nematicide were placed on a turntable in a spray hood and sprayed with 50 ml of a water/acetone solution of the appropriate amount of candidate nematicide to provide application rates of 2000 ppm or lower. The soil surface in each pot was covered during spraying. After treatment with the candidate nematicide, the test plants were dried in a lighted drying chamber, then placed in a growth chamber, where they were maintained at 25° C. for three days. The soil of each test plant was inoculated with root-knot nematodes by incorporation of the inoculum into the top of 5 cm of soil. The test plants were returned to the growth chamber where they were maintained for 2-3 weeks prior to evaluation. Table 7 (appended) shows that compound 26 provided 100% control of the root-knot nematode at 2000 ppm application rate.

TABLE 1

Imidodithiocarbonates

| Compd No. | R | R¹ | Root-knot Nematicide Activity |
|---|---|---|---|
| 1 | K | CN | A++ |
| 2 | —CH₃ | CN | A+++ |
| 3 | —C₂H₅ | CN | A+++ |
| 4 | —C₃H₇ | CN | A+++ |
| 5 | —C₈H₁₇ | CN | A+++ |
| 6 | —CH₂CH(CH₃)₂ | CN | A+ |
| 7 | —CH₂CH(C₂H₅)₂ | CN | A++ |
| 8 | —CH₂CH₂CH(CH₃)₂ | CN | A+++ |
| 9 | —CH₂—<small>△</small> (cyclopropyl) | CN | A+++ |
| 10 | —CH₂CH=CH₂ | CN | A+ |
| 11 | —CH₂CH₂CH=CH₂ | CN | A+++ |
| 12 | —(CH₂)₄CH=CH₂ | CN | A+++ |
| 13 | —CH₂C≡CH | CN | A+ |
| 14 | —CH₂CH₂F | CN | A+ |
| 15 | —CH₂CH=CCl₂ | CN | A++ |
| 16 | —CH₂CH=CBr₂ | CN | A+++ |
| 17 | —CH₂CH₂CF=CF₂ | CN | A+++ |
| 18 | 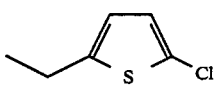 | CN | A+++ |
| 19 | —2-CH₂C₆H₄F | CN | A |
| 20 | —2,6-CH₂C₆H₃F₂ | CN | A+++ |
| 21 | —2,6-CH₂C₆H₃Cl₂ | CN | |
| 22 | —CH₂C₆F₅ | CN | A++ |
| 23 | 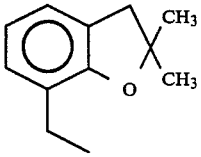 | CN | A+ |
| 24 | 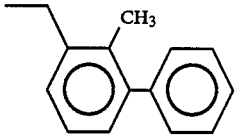 | CN | A+ |
| 25 | 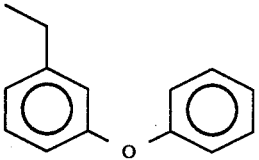 | CN | A+ |
| 26 | —CH₂S—4-C₆H₄Cl | CN | A+++ |
| 27 | —C₂H₄SC₆H₅ | CN | A+++ |
| 28 | —PO(OCH₂CH₃)₂ | CN | A+++ |
| 29 | —PS(OCH₂CH₃)₂ | CN | A++ |
| 30 | —CH₃ | CH₃ | A++ |
| 31 | —CH₃ | 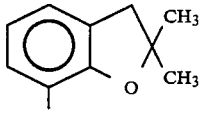 | — |

TABLE 1-continued

Imidodithiocarbonates $$R-S-C(=N-R^1)-S-CH_2CH_2-CF=CF_2$$

| Compd No. | R | R¹ | Root-knot Nematicide Activity |
|---|---|---|---|
| 32 | —C₂H₅ | " | |
| 33 | —CH₂-cyclopropyl | " | |
| 34 | 2-ethyl-5-chlorothiophene | " | A |
| 35 | —CH₂S—4-C₆H₄Cl | " | |
| 36 | —CH₃ | 5-methyl-1,3,4-thiadiazol-2-yl | A |
| 37 | —CH₃ | 5-trifluoromethyl-1,3,4-thiadiazol-2-yl | A++ |
| 38 | —CH₃ | benzothiazol-2-yl | |
| 39 | —CH₃ | 4-C₆H₄Cl | A |
| 40 | —CH₃ | 4-C₆H₄OCF₃ | A |
| 41 | —CH₂-cyclopropyl | 5-methyl-1,3,4-thiadiazol-2-yl | A |
| 42 | —CH₂-cyclopropyl | 5-trifluoromethyl-1,3,4-thiadiazol-2-yl | A |
| 43 | —CH₂-cyclopropyl | 4-C₆H₄Cl | A |
| 44 | —CH₂-cyclopropyl | 4-C₆H₅OCF₃ | |
| 45 | —C₂H₄CF=CF₂ | 5-chloro-2-methylpyridyl | |
| 46 | —C₂H₄CF=CF₂ | 2-chloropyridyl | A |
| 47 | —CH₂S—4-C₆H₄Cl | 4-C₆H₄Cl | A |
| 48 | —CH₂S—4-C₆H₄Cl | 4-C₆H₅OCF₃ | A |
| 49 | —CH₂CH₂CH₂Cl | CN | A++ |

TABLE 1-continued

Imidodithiocarbonates $$R-S-C(=N-R^1)-S-CH_2CH_2-CF=CF_2$$

| Compd No. | R | R¹ | Root-knot Nematicide Activity |
|---|---|---|---|
| 50 | —CH₂—(2,2-dichlorocyclopropyl) | CN | A+++ |
| 51 | —CH₂—cyclobutyl | CN | A+++ |
| 52 | —CH₂—(2,2,3,3-tetrafluorocyclobutyl) | CN | A+++ |
| 53 | —CH₂—C₆H₅ | CN | A+ |
| 54 | —CH₂—(3-fluorophenyl) | CN | |
| 55 | —CH₂—(4-fluorophenyl) | CN | A++ |
| 56 | —CH₂—(2-nitrophenyl) | CN | |
| 57 | —CH₂—(4-nitrophenyl) | CN | A+++ |
| 58 | —CH₂—(3,5-dimethylisoxazol-4-yl) | CN | |
| 59 | —CH₂—(3-(2-thienyl)isoxazol-5-yl) | CN | A+++ |

TABLE 1-continued

Imidodithiocarbonates $$R-S-C(=N-R^1)-S-CH_2CH_2-CF=CF_2$$

| Compd No. | R | $R^1$ | Root-knot Nematicide Activity |
|---|---|---|---|
| 60 | —CH₂Si(CH₃)₂(CH=CH₂) | CN | A+ |
| 61 | —CH₂Si(CH₃)₂(C₆H₅) | CN | |
| 62 | —CH₂Si(OCH₂CH₃)₂(CH₃) | CN | A++ |
| 63 | —CH₂C(=O)CH₂CH₃ | CN | A+ |
| 64 | —CH₂C(=O)(4-Cl-C₆H₄) | CN | |
| 65 | —CH₂CH₂(4-Cl-C₆H₄) | CN | |
| 66 | —CH₂CH₂(2-CF₃-C₆H₄) | CN | A++ |
| 67 | —CH₂CH₂OCH₂CH₃ | CN | A+++ |
| 68 | —CH₂(CH₂)₃OCH₃ | CN | A+++ |
| 69 | —CH₂CH₂O(4-Br-C₆H₄) | CN | |
| 70 | —CH₂CH₂S(CH₂)₂CH₃ | CN | A+++ |
| 71 | —CH₂CH₂S(C₆H₅) | CN | A+++ |
| 72 | —CH₂CH₂S(4-Cl-C₆H₄) | CN | A++ |
| 73 | —CH₂CH₂Si(CH₃)₃ | CN | A+++ |
| 74 | —CH₂CH₂OC(=O)OCH₃ | CN | A+++ |

TABLE 1-continued

Imidodithiocarbonates $$R-S-C(=N-R^1)-S-CH_2CH_2-CF=CF_2$$

| Compd No. | R | R¹ | Root-knot Nematicide Activity |
|---|---|---|---|
| 75 | —CH₂CH₂CH₂—C₆H₅ | CN | |
| 76 | —CH₂CH₂C(CN)(C₆H₅)₂ | CN | A |
| 77 | —CH₂(CH₂)₂CH=CH₂ | CN | A++ |
| 78 | —CH₂(CH₂)₅CH=CH₂ | CN | A++ |
| 79 | —CH₂CH=C(CH₃)₂ | CN | A+++ |
| 80 | —CH₂CH₂CH=C(Cl)(cyclopropyl) | CN | |
| 81 | —CH₂CH=CH—C₆H₅ | CN | |
| 82 | —CH₃ | —CH₂CF₂CF₃ | |
| 83 | —CH₂—cyclopropyl | —CH₂CF₂CF₃ | |
| 84 | —CH₂CH₂CF=CF₂ | —CH₂CF₂CF₃ | |
| 85 | —CH₂S—C₆H₄—Cl | —CH₂CF₂CF₃ | |
| 86 | —CH₃ | cyclopropyl | A++ |
| 87 | —CH₂—cyclopropyl | cyclopropyl | |
| 88 | —CH₂CH₂CF=CF₂ | cyclopropyl | A |
| 89 | —CH₂S—C₆H₄—Cl | cyclopropyl | |
| 90 | —CH₃ | —C₆H₄—Cl | |

TABLE 1-continued

Imidodithiocarbonates $$R-S-C(=N-R^1)-S-CH_2CH_2-CF=CF_2$$

| Compd No. | R | R¹ | Root-knot Nematicide Activity |
|---|---|---|---|
| 91 | —CH₃ | 2-F-C₆H₄— | |
| 92 | —CH₂-cyclopropyl | 2-F-C₆H₄— | |
| 93 | —CH₂S-C₆H₄-4-Cl | 2-F-C₆H₄— | A |
| 94 | —CH₃ | —CH₂-C₆H₄-4-Cl | A+++ |
| 95 | —CH₂-cyclopropyl | —CH₂-C₆H₄-4-Cl | A+++ |
| 96 | —CH₂S-C₆H₄-4-Cl | —CH₂-C₆H₄-4-Cl | A+++ |
| 97 | —CH₃ | —CH₂CH₂-C₆H₄-4-Cl | A |
| 98 | —CH₂S-cyclopropyl | —CH₂CH₂-C₆H₄-4-Cl | |
| 99 | —CH₂S-C₆H₄-4-Cl | —CH₂CH₂-C₆H₄-4-Cl | |
| 100 | —CH₂-cyclopropyl | —CH₂CH₂N(CH₃)₂ | |
| 101 | —CH₂CH₂CF=CF₂ | —CH₂CH₂N(CH₃)₂ | |
| 102 | —CH₂S-C₆H₄-4-Cl | —CH₂CH₂N(CH₃)₂ | |

TABLE 1-continued
Imidodithiocarbonates

R—S—C(=N—R¹)—S—CH₂CH₂CF=CF₂

| Compd No. | R | R¹ | Root-knot Nematicide Activity |
|---|---|---|---|
| 103 | —CH₃ | 3-pyridyl | A+ |
| 104 | —CH₂-cyclopropyl | 3-pyridyl | |
| 105 | —CH₂S-(4-chlorophenyl) | 3-pyridyl | |
| 106 | —CH₂CH₂CF=CF₂ | 4,5-dimethyloxazol-2-yl | A+ |
| 107 | —CH₂CH₂CF=CF₂ | 4,5-dihydrothiazol-2-yl | A+++ |

TABLE 1a
Dithiocarbamates

R³R²N—C(=S)—S—CH₂CH₂CF=CF₂

| Cmpd No. | R² | R³ | Root-knot Nematicide Activity |
|---|---|---|---|
| A1 | H | CH₂CF₂CF₃ | A+ |
| A2 | H | 4,5-dimethyloxazol-2-yl | A+++ |
| A3 | H | 4,5-dihydrothiazol-2-yl | A+++ |
| A4 | H | benzothiazol-2-yl | A++ |
| A5 | H | 4-phenylthiazol-2-yl | A |
| A6 | H | 5-methyl-1,3,4-thiadiazol-2-yl | A |
| A7 | H | 5-trifluoromethyl-1,3,4-thiadiazol-2-yl | A |
| A8 | H | 3-pyridyl | A+++ |
| A9 | H | 3-fluorophenyl | A |

TABLE 1a-continued

Dithiocarbamates $$R^3R^2N-C(=S)-S-CH_2CH_2-C(F)=CF_2$$

| Cmpd No. | R² | R³ | Root-knot Nematicide Activity |
|---|---|---|---|
| A10 | H | 4-Cl-C₆H₄ | A+++ |
| A11 | H | 4-OCF₃-C₆H₄ | A+++ |
| A12 | H | 2,2-dimethyl-7-methyl-2,3-dihydrobenzofuran-yl | A |
| A13 | H | 4-CH₂C₆H₄Cl | A+++ |
| A14 | H | —4-CH₂CH₂C₆H₄Cl | A |
| A15 | CH₃ | (CH₃)C=N-N=C(CH₃)-S- | A+++ |
| A16 | CH₃ | (CH₃)C=N-N=C(CF₃)-S- | — |
| A17 | H | —CH(CH₃)CH₂CH₃ | A |
| A18 | H | —C(CH₃)₃ | |
| A19 | H | CH₂CF₃ | |
| A20 | H | cyclopropyl | A+ |
| A21 | H | cyclopentyl | A |
| A22 | H | cyclohexyl | A |
| A23 | H | —CH₂-cyclopropyl | A+ |
| A24 | H | phenyl | A+ |
| A25 | CH₃ | phenyl | A+++ |
| A26 | H | —CH₂CH₂N(CH₃)₂ | A |
| A27 | H | 2-(4-Cl)pyridyl | A+ |

TABLE 2

C. Elegans Nematode Screen - Rate: 5 ppm

| Compound No. | Percent Inhibition of Reproduction | Percent Mortality |
|---|---|---|
| 2 | 50 | 0 |
|  | 100 | 75 |
| 20 | 50 | 0 |
| 47 | 100 | 75 |
| 48 | 50 | 50 |
| 54 | 63 | 0 |
| 57 | 100 | 100 |
| 64 | 100 | 88 |
| 70 | 50 | 0 |
| 74 | 100 | 25 |
| 80 | 25 | 0 |
| 82 | 25 | 0 |
| 94 | 38 | 0 |
| 96 | 100 | 100 |
| 99 | 100 | 25 |
| A7 | 50 | 0 |
| A8 | 100 | 88 |
| A10 | 100 | 100 |
| A11 | 100 | 100 |
| A13 | 100 | 100 |
| A14 | 100 | 100 |

TABLE 3

C. Elegans Nematode Rate Evaluation

| Compound No. | Rate (ppm) | Percent Inhibition of Reproduction | Percent Mortality |
|---|---|---|---|
| 64 | 5 | 100 | 50 |
|  | 2.5 | 100 | 8 |
|  | 1.25 | 25 | 0 |
| 96 | 5 | 100 | 100 |
|  | 2.5 | 100 | 50 |
|  | 1.25 | 17 | 0 |
| 99 | 5 | 100 | 92 |
|  | 2.5 | 92 | 0 |
|  | 1.25 | 0 | 0 |
| A10 | 5 | 100 | 100 |
|  | 2.5 | 100 | 42 |
|  | 1.25 | 0 | 0 |
| A11 | 5 | 100 | 100 |
|  | 2.5 | 100 | 58 |
|  | 1.25 | 42 | 0 |
| A13 | 5 | 100 | 100 |
|  | 2.5 | 100 | 75 |
|  | 1.25 | 25 | 0 |
| A14 | 5 | 100 | 100 |
|  | 2.5 | 100 | 100 |
|  | 1.25 | 100 | 92 |

TABLE 4

| Stunt Nematode Screen | | |
|---|---|---|
| Compd. No. | Rate (ppm) | Percent Control |
| 2 | 5 | 90 |
| 3 | 5 | 58 |
| 9 | .5 | 85 |
| 17 | 5 | 50 |
| 18 | 5 | 68 |
| 20 | 5 | 48 |
| 26 | 5 | 55 |

TABLE 5

| Lesion Nematode Screen | | |
|---|---|---|
| Compd. No. | Rate (ppm) | Percent Control |
| 2 | 2.5 | 10 |
|   | 5 | 78 |
| 3 | 2.5 | 10 |
|   | 2.5 | 70 |
| 9 | 5 | 49 |
| 18 | 2.5 | 49 |
| 26 | 2.5 | 61 |

TABLE 6

| Cyst Nematode Screen | | |
|---|---|---|
| Compd. No. | Rate (ppm) | Percent Control |
| 3 | 5 | 15 |
| 9 | 5 | 66 |
| 26 | 5 | 4 |

TABLE 7

| Root-knot Nematode Systemic Screen | | |
|---|---|---|
| Compd. No. | Rate (ppm) | Percent Control |
| 1 | 2000 | 17 |
| 9 | 2000 | 17 |
| 26 | 2000 | 100 |
| 30 | 2000 | 8 |

We claim:

1. S-trifluorobutenyl compounds of the formula

and salts thereof,
wherein X is $R^1N$ or S and Y is RS or $R^3R^2N$;
wherein R is a metal or a radical selected from alkyl, cycloalkylalkyl, halocycloalkylalkyl, alkenyl, haloalkyl, haloalkenyl, alkynyl, alkoxyalkyl, alkylthioalkyl, alkoxycarbonylalkyl, halophenoxyalkyl, phenylalkyl, halophenylalkyl, nitrophenylalkyl, haloalkylphenylalkyl, [2-methyl-(1,1'-biphenyl)-3-yl]methyl, 3-phenoxybenzyl, phenylthioalkyl and halophenylthioalkyl;
wherein $R^1$ is alkyl, cycloalkyl, cyano, halophenyl, halophenylalkyl or haloalkoxyphenyl;
wherein $R^2$ is hydrogen or alkyl; and
wherein $R^3$ is cycloalkylalkyl, dialkylaminoalkyl, halophenyl, halophenylkalkyl or haloalkoxyphenyl;
said alkyl and alkoxy groups having 1–12 carbon atoms; said cycloalkyl groups having 3–8 carbon atoms; and said alkenyl and alkynyl groups having 2–12 carbon atoms;
provided that:

when X is S, Y is $R^3R^2N$,
when X is $R^1N$, Y is RS,
  $R^1$ is other than alkyl and
  R is other than haloalkenyl; and
when X is $R^1N$ where $R^1$ is CN and Y is RS,
  R is other than alkali metal.

2. Compounds of claim 1 wherein X is S and Y is $R^3R^2N$.

3. Compounds of claim 2 wherein $R^2$ is hydrogen and $R^3$ is haloalkoxyphenyl.

4. Compounds of claim 2 wherein $R^2$ is hydrogen and $R^3$ is halophenyl.

5. Compounds of claim 2 wherein $R^2$ is hydrogen and $R^3$ is halophenylalky.

6. Compounds of claim 1 wherein X is $R^1N$ and Y is RS.

7. A compound of claim 6 which is ethyl(3,4,4-trifluoro-3-butenyl)cyanoimidodithiocarbonate.

8. A compound of claim 6 which is propyl(3,4,4-trifluoro-3-butenyl)cyanoimidodithiocarbonate.

9. A compound of claim 6 which is 3-methylbutyl(3,4,4-trifluoro-3-butenyl)cyanoimidodithiocarbonate.

10. A compound of claim 6 which is cyclopropylmethyl(3,4,4-trifluoro-3-butenyl)cyanoimidodithiocarbonate.

11. A compound of claim 6 which is 5-hexenyl(3,4,4-trifluoro-3-butenyl)cyanoimidodithiocarbonate.

12. A method of controlling nematodes which comprises applying to the locus where control is desired a nematicidally effective amount of a compound of claim 1.

13. A method of controlling nematodes which comprises applying to the locus where control is desired a nematicidally effective amount of a compound of claim 2.

14. A method of controlling nematodes which comprises applying to the locus where control is desired a nematicidally effective amount of a compound of claim 6.

15. A method of controlling nematodes which comprises applying to the locus where control is desired a nematicidally effective amount of a compound of claim 7.

16. A method of controlling nematodes which comprises applying to the locus where control is desired a nematicidally effective amount of a compound of claim 8.

17. A method of controlling nematodes which comprises applying to the locus where control is desired a nematicidally effective amount of a compound of claim 9.

18. A method of controlling nematodes which comprises applying to the locus where control is desired a nematicidally effective amount of a compound of claim 10.

19. A method of controlling nematodes which comprises applying to the locus where control is desired a nematicidally effective amount of a compound of claim 11.

20. A nematicidal composition comprising a nematicidally effective amount of a compound of claim 1 in an agriculturally acceptable carrier.

21. A nematicidal composition comprising a nematicidally effective amount of a compound of claim 2 in an agriculturally acceptable carrier.

22. A nematicidal composition comprising a nematicidally effective amount of a compound of claim 6 in an agriculturally acceptable carrier.

* * * * *